United States Patent
Ryu et al.

(10) Patent No.: US 10,278,795 B2
(45) Date of Patent: May 7, 2019

(54) DENTAL IMPLANT ABUTMENT AND METHOD FOR MANUFACTURING SAME

(75) Inventors: Jae Ho Ryu, Busan (KR); Moo Young Park, Busan (KR); Byung Kook Kim, Busan (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 0 days.

(21) Appl. No.: 14/007,921

(22) PCT Filed: Feb. 7, 2012

(86) PCT No.: PCT/KR2012/000876
§ 371 (c)(1),
(2), (4) Date: Sep. 26, 2013

(87) PCT Pub. No.: WO2012/134051
PCT Pub. Date: Oct. 4, 2012

(65) Prior Publication Data
US 2014/0017632 A1    Jan. 16, 2014

(30) Foreign Application Priority Data
Mar. 28, 2011   (KR) ........................ 10-2011-0027569

(51) Int. Cl.
*A61C 8/00*       (2006.01)
*A61C 13/083*   (2006.01)
(Continued)

(52) U.S. Cl.
CPC ............ *A61C 8/0051* (2013.01); *A61C 8/005* (2013.01); *A61C 8/006* (2013.01); *A61C 8/0048* (2013.01);
(Continued)

(58) Field of Classification Search
CPC ..... A61C 8/0048; A61C 8/005; A61C 8/0051; A61C 8/006; A61C 13/083
(Continued)

(56) References Cited

U.S. PATENT DOCUMENTS 4,988,298 A   1/1991 Lazzara et al.
5,180,303 A   1/1993 Hornburg et al.
(Continued)

FOREIGN PATENT DOCUMENTS

EP    0868890 A2    10/1998
JP    2006-520248 A   9/2006
(Continued)

OTHER PUBLICATIONS

KIPO NOA dated Dec. 2, 2012; Appln. No. 10-2011-0027569.
Supplementary European Search Report dated Dec. 17, 2014; Appln. No. EP 12 76 5632.

*Primary Examiner* — Edward Moran
(74) *Attorney, Agent, or Firm* — Ladas & Parry LLP

(57) ABSTRACT

Provided are a dental implant abutment and a method of manufacturing the same, and more particularly, a dental implant abutment which forms an outer appearance of an artificial tooth, supports a porcelain prosthesis that is formed of a porcelain, and couples to and fixedly combines with a fixture. The dental implant abutment includes: a first part having a coupling structure that corresponds to an inner structure of the fixture, so that the first part couples to the fixture; a second part that extends upward from the first part and contacts gums; and a third part extending upward from the second part, having an outer circumferential surface which includes a side surface and a top surface, with a porcelain prosthesis attached to the outer circumferential surface, and including a shape in which a concave part, inwardly recessed, is formed on the side and a horizontal (Continued)

cross-sectional area increases in an upward direction from the concave part.

13 Claims, 4 Drawing Sheets

(51) Int. Cl.
*A61C 13/00* (2006.01)
*A61K 6/02* (2006.01)
*A61K 6/04* (2006.01)
*A61K 6/08* (2006.01)

(52) U.S. Cl.
CPC ........ *A61C 13/0006* (2013.01); *A61C 13/083* (2013.01); *A61K 6/0205* (2013.01); *A61K 6/046* (2013.01); *A61K 6/08* (2013.01)

(58) Field of Classification Search
USPC ...................................... 433/172–176, 201.1
See application file for complete search history.

(56) References Cited

U.S. PATENT DOCUMENTS

| | | | | |
|---|---|---|---|---|
| 5,542,847 A | * | 8/1996 | Margulies | ............... 433/173 |
| 5,674,069 A | * | 10/1997 | Osorio | ............... 433/172 |
| 5,873,721 A | * | 2/1999 | Willoughby | ...... A61C 8/0001 |
| | | | | 433/172 |
| 5,934,906 A | * | 8/1999 | Phimmasone | ...... A61C 8/0001 |
| | | | | 433/172 |
| 2001/0021498 A1 | | 9/2001 | Osorio et al. | |
| 2007/0298379 A1 | * | 12/2007 | D'Alise | ............ A61C 8/0025 |
| | | | | 433/174 |
| 2010/0119995 A1 | * | 5/2010 | Grant et al. | ............ 433/174 |

FOREIGN PATENT DOCUMENTS

| | | |
|---|---|---|
| KR | 100730344 B1 | 6/2007 |
| KR | 100795645 B1 | 1/2008 |
| KR | 1020090048078 A | 5/2009 |
| KR | 1020120010475 A | 2/2012 |
| WO | 2004/080327 A1 | 9/2004 |

* cited by examiner (a)

(b)

(d)

(c)

(e)

(f)

DENTAL IMPLANT ABUTMENT AND METHOD FOR MANUFACTURING SAME

CROSS-REFERENCE TO RELATED APPLICATIONS

This application is the national stage application of International Application No. PCT/KR2012/000876, filed Feb. 7, 2012, which claims priority to Korean Application No. 10-2011-027569, filed on Mar. 28, 2011.

TECHNICAL FIELD

One or more aspects of the present invention relate to a dental implant abutment and a method of manufacturing the same, and more particularly, to a dental implant abutment in which the dental implant abutment and an inner crown are formed together as one body, so that the time and cost for forming a whole artificial tooth may be saved, and a method of manufacturing the same.

BACKGROUND ART

An implant means a substitute for recovering lost human tissue. In dentistry, an implant generally means a substitute for recovering an original function of a lost tooth by planting and integrating a fixture into the alveolar bone, from which a natural dental root is missing, so as to replace a dental root of the lost tooth, and fixing an artificial tooth to the fixture.

Such dental implants may be classified according to a method of coupling an artificial tooth to a dental root. A screw-type implant, which is one of the dental implants, is manufactured by using a binding force of a screw. Conventionally, a screw-type implant or implant assembly consists of a fixture, an abutment and a prosthesis.

As shown in FIG. 1, a structure of a conventional dental implant prosthesis 100 includes an outer crown 110 that is formed of porcelain, and an inner crown 120 that is employed as a lower structure of the outer crown 110 and supports the outer crown 110. The inner crown 120 may be formed of various materials such as a gold (Au) alloy, a nickel (Ni)-chrome (Cr) alloy, zirconium (Zr), alumina, or titanium (Ti). The inner crown 120 may be manufactured by using a casting or cutting method, according to characteristics of each material. The inner crown 120 is deposited, and thus coupled to the outer crown 110 by using a mechanical and chemical mechanism.

An abutment 130 is conventionally formed of Ti or Zr, and is coupled to the inner crown 120 by using a dental adhesive. The abutment 130 is connected to an implant 140 that is installed in a mouth of a patient. The abutment 130 functions to support a prosthesis that is formed of the inner crown 120 and the outer crown 110.

If the outer crown 110 is formed of porcelain, instead of gold or another metal material, an artificial tooth may have a shape and color that are similar to a natural tooth. However, when used as the outer crown 110, the porcelain needs to have an overall even thickness of 0.3 to 3 mm due to its material characteristics, as shown in FIG. 2. An uneven thickness of porcelain may easily cause a fracture in porcelain. Particularly, if porcelain has a heavy thickness, a fracture may be easily caused in porcelain. Thus, an inner crown, which forms an internal structure of porcelain, needs to be precisely designed so that the porcelain may have an even thickness.

However, if an inner crown is manufactured by using a conventional casting method, it is not easy to precisely manufacture the inner crown. This is because since the casting method includes manufacturing a cast and melting metal into the cast, it is difficult to precisely manufacture an inner crown by using the casting method. Additionally, shrinkage may be caused in a hardening process that is performed after casting. Particularly, the casting may be affected by a lot of factors, such that the casting method greatly depends on the skill of a worker. Furthermore, there is a possibility that the casting may fail, or an environmental pollution may be caused.

Additionally, it takes about 8 hours for each cycle to manufacture an inner crown. Accordingly, it takes a long time to manufacture an inner crown, and thus, a manufacturing cost is increased.

DETAILED DESCRIPTION OF THE INVENTION

Technical Problem

In order to solve the problems, described above, one or more aspects of the present invention provide a dental implant abutment in which the dental implant abutment and an inner crown are formed together as one body, so that manufacturing time and cost may be saved and a possibility of a manufacturing failure is reduced, and a method of manufacturing the same.

Technical Solution

According to an aspect of the present invention, there is provided a dental implant abutment, which forms an outer appearance of an artificial tooth, supports a porcelain prosthesis that is formed of porcelain, and couples to and fixedly combines with a fixture, the dental implant abutment including: a first part having a coupling structure that corresponds to an inner structure of the fixture, so that the first part couples to the fixture; a second part that extends upward from the first part and contacts gums; and a third part extending upward from the second part, having an outer circumferential surface which includes a side and a top surface, with the porcelain prosthesis attached to the outer circumferential surface, and including a shape in which a concave part, inwardly recessed, is formed in the side and a horizontal cross-sectional area increases in an upward direction from the concave part.

The third part may have an irregular and asymmetric outer appearance.

The third part may have a shape in which a horizontal cross-sectional area increases downward from the concave part, and a maximum horizontal cross-sectional area of the third part, which is disposed on the concave part, may be greater than a maximum horizontal cross-sectional area of the third part, which is disposed below the concave part.

The maximum horizontal cross-sectional area of the third part may be greater than a maximum horizontal cross-sectional area of the second part.

A thickness of an outer appearance of the third part may be less than a thickness of a corresponding part of an outer appearance of an artificial tooth by 0.1 mm to 3 mm.

The porcelain prosthesis and the third part may be directly attached to each other in a porcelain furnace by using a sintering process.

The outer appearance of the third part may be manufactured by using a computer-aided design (CAD) program.

The first part may include a connection part that may have a cross-section in the form of one from among an octagon, a hexagon, a rectangle, and a circle.

The dental implant abutment may be formed of one material from among titanium (Ti), a Ti alloy, a cobalt (Co)-chrome (Cr)-molybdenum (Mo) alloy, a nickel (Ni)—Cr alloy, a gold (Au) alloy, zirconium (Zr), aluminum (Al) oxide, and a polymer.

A boundary between the second part and the third part may have an irregular curved structure A shape of the third part may be formed manually by using dental wax and is obtained by using three-dimensional (3D) scanning.

A shape of the third part may be defined by a shape of an artificial tooth.

The porcelain prosthesis may be manufactured by using a method of being sintered and attached to the third part.

According to an aspect of the present invention, there is provided a dental implant abutment, which forms an outer appearance of an artificial tooth, supports a porcelain prosthesis that is formed of porcelain, and couples to and fixedly combines with a fixture, the dental implant abutment including: a first part having a coupling structure that corresponds to an inner structure of the fixture, so that the first part couples to the fixture; a second part that is connected to the first part and contacts gums; and a third part extending upward from the second part, having an outer circumferential surface which includes a side and a top surface, with a porcelain prosthesis attached to the outer circumferential surface, wherein a thickness of an outer appearance of the third part is less than a thickness of a corresponding part of an outer appearance of an artificial tooth by 0.1 mm to 3 mm.

According to an aspect of the present invention, there is provided a method of manufacturing a dental implant abutment, the method including: impression taking for patterning the mouth of a patient to take an impression; model manufacturing for manufacturing a model of the patient's mouth by using the taken impression; image generation for creating a 3D image by scanning the model of the patient's mouth; artificial tooth creation for creating an outer appearance of an artificial tooth by using the generated image; abutment designing for obtaining design information about the abutment by removing 0.1 to 3 mm of an outer appearance of an artificial tooth along an outer circumferential surface; and abutment manufacturing for manufacturing the implant abutment by cutting and tooling a base material according to the design information about the abutment.

The artificial tooth creation may be performed by using a computer-aided design (CAD) program.

The abutment manufacturing may include transmitting the design information about the abutment to a computer-aided manufacturing (CAM) program; creating numerical control (NC) data for tooling the abutment by using the CAM program; and tooling the abutment based on the NC data by using a cutting machine.

The abutment may include an outer circumferential surface which includes a side and a top surface, with a porcelain prosthesis attached to the outer circumferential surface, and the abutment may have a shape in which a concave part, inwardly recessed, is formed on the side and a horizontal cross-sectional area increases upward from the concave part.

Advantageous Effects

With regard to a dental implant abutment in the present invention, an inner crown is manufactured as one body with the dental implant abutment, and thus, disadvantages, which may be caused by inconvenient working conditions, a cost increase, an increase in a possibility of manufacturing failure, and environmental pollution, may be solved.

Particularly, a consistent quality of a porcelain prosthesis may be obtained regardless of the skill of a worker.

MODE OF THE INVENTION

Figure 1:
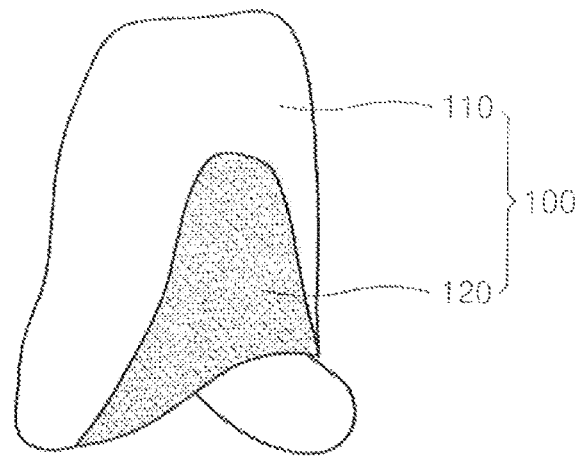
FIG. 1 is an image illustrating a prosthesis that is used for a conventional dental implant.
Figure 2:
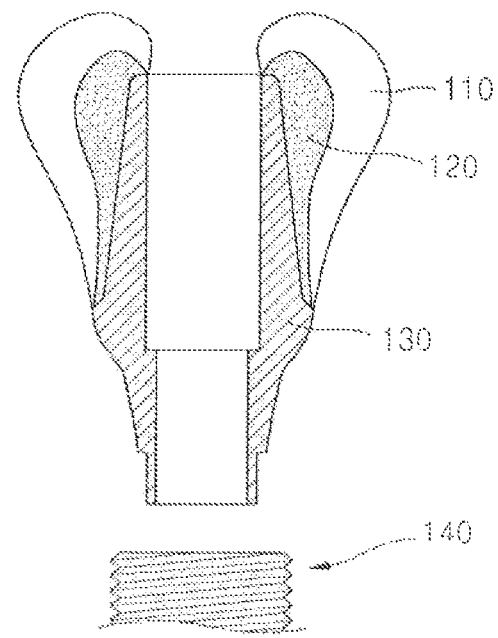
FIG. 2 is a diagram illustrating a conventional dental implant abutment shown in FIG. 1.
Figure 3:
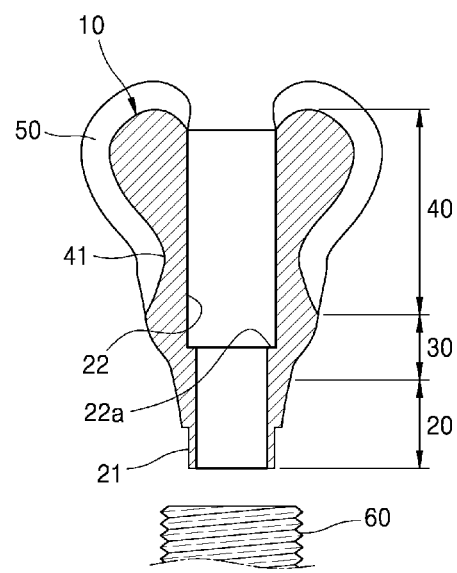
FIG. 3 is a diagram illustrating a dental implant abutment according to an embodiment of the present invention.

Hereinafter, according to an embodiment of the present invention, a dental implant abutment 10 will be described in detail with reference to the attached drawings.

According to an embodiment of the present invention, main characteristics of the dental implant abutment 10 are such that an inner crown, which was conventionally manufactured separately, is formed as one body with the dental implant abutment 10, and thus, a manufacturing time may be reduced. Additionally, since the inner crown is manufactured by using machine tooling when the dental implant abutment 10 is manufactured, the precision of the inner crown may be improved.

The dental implant abutment 10 supports a porcelain prosthesis 50 that is formed of porcelain that defines an outer appearance of an artificial tooth and is coupled to and fixedly combined with a fixture.

The dental implant abutment 10 includes a first part 20, a second part 30, and a third part 40. The dental implant abutment 10 may be formed of one material from among titanium (Ti), a Ti alloy, a cobalt (Co)-chrome (Cr)-molybdenum (Mo) alloy, a nickel (Ni)—Cr alloy, a gold (Au) alloy, zirconium (Zr), aluminum (Al) oxide, and a polymer.

The first part 20 has a coupling structure that corresponds to an internal structure of a fixture 60, so as to form a lower part of the dental implant abutment 10. The first part 20 is formed to have a tapered shape in which an outer diameter decreases from an upper part to a lower part. A connection part 21 is formed on the lower part of the first part 20. The connection part 21 may have a cross-section in the form of one from among an octagon, a hexagon, a rectangle, and a circle. If the connection part 21 has a cross section of an octagon or a hexagon, when inserted inside the fixture 60, the connection part 21 may function to prevent the dental implant abutment 10 from relatively rotating against the fixture 60.

A hollow hole 22, which communicates upwards and downwards, is formed at a center of the first part 20. The hollow hole 22 is a hole that extends from an upper end of the third part 40 to a lower end of the first part 20. A coupling screw (not illustrated) for coupling the dental implant abutment 10 to the fixture 60 may be inserted inside the hollow hole 22.

The second part 30 is connected to the first part 20 as one body, and extends upwards from the first part 20. When coupled to the fixture 60, the second part 30 is a part which protrudes from the fixture 60. An outer circumferential surface of the second part 30 contacts a gum. The second part 30 approximately forms a central part of the dental implant abutment 10.

The second part 30 is formed to have a shape in which an outer diameter of the second part 30 gradually increases from the first part 20. The hollow hole 22, which extends from the first part 20, is formed inside the second part 30. A step 22a, in which an inner diameter is decreased, is formed in an area of the hollow hole 22 that approximately corresponds to the second part 30. A coupling screw may be stuck in the step 22a.

The third part 40 has an irregular and asymmetric outer appearance, instead of a standardized circular cross-section. The third part 40 has an outer circumferential surface that extends upward from the second part 30 and includes a side and an upper surface. Additionally, since the third part 40 has an irregular shape, a boundary between the second part 30 and the third part 40 may have an irregular curved structure. The third part 40 forms an upper part of the dental implant abutment 10, and the porcelain prosthesis 50 is attached to the outer circumferential surface of the dental implant abutment 10.

A horizontal cross-sectional area of a side of the third part 40 is gradually decreased upward from the second part 30, and then, is gradually increased. An area, in which a cross-sectional is increased, and then, decreased, has a concave part 41. The concave part 41 has an inwardly recessed shape.

A maximum horizontal cross-sectional area of the third part 40, which is disposed on an upper part of the concave part 41, may be desirably greater than a maximum horizontal cross-sectional area of the third part 40, which is disposed on a lower part of the concave part 41.

Additionally, a maximum horizontal cross-sectional area of the third part 40 may be desirably greater than a maximum horizontal cross-sectional area of the second part 30.

An outer appearance of the third part 40 has a shape in which a thickness of 0.1 to 3 mm is removed from an outer appearance of an artificial tooth, which is a final outer appearance of a porcelain prosthesis. Desirably, the outer appearance of the third part 40 may have a shape in which a thickness of 0.3 to 3 mm is removed from the outer appearance of an artificial tooth. Accordingly, about 0.3 to 3 mm of porcelain may be attached to an outer circumferential surface of the third part 40. As such, porcelain may have an even thickness along the outer circumferential surface of the third part 40. Thus, a fracture may not be easily generated.

Desirably, the porcelain prosthesis 50 may be directly attached to the third part 40. The porcelain prosthesis 50 may directly contact the third part 40, without having to, for example, insert an inner crown between the porcelain prosthesis 50 and the dental implant abutment 10 as in a conventional technology. The third part 40 is formed manually by using dental wax, and is obtained by using three-dimensional (3D) scanning. An outer appearance of the third part 40 may be designed by using a computer-aided design (CAD) program, and precisely cut by using a computer-aided manufacturing (CAM) program and a cutting tool. A shape of the third part 40 may be determined according to a shape of an artificial tooth.

The porcelain prosthesis 50, attached to the third part 40, may be directly attached to the third part 40 in a porcelain furnace by using a sintering process.

In the present invention, a dental implant abutment is manufactured as follows: Specifically, the manufacturing of the dental implant abutment 10 includes impression taking S100, model manufacturing S200, image generation S300, artificial tooth creation S400, abutment designing S500, and abutment manufacturing S600.

In the impression taking S100, an impression is taken by patterning the mouth of a patient.

In the model manufacturing S200, a model of the patient's mouth is manufactured by using the taken impression.

Figure 4:
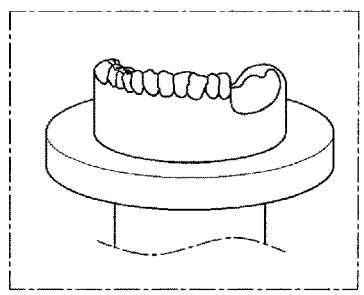
FIG. 4A through 4F are diagrams illustrating a method of manufacturing the dental implant abutment of FIG. 3.
Figure 4:
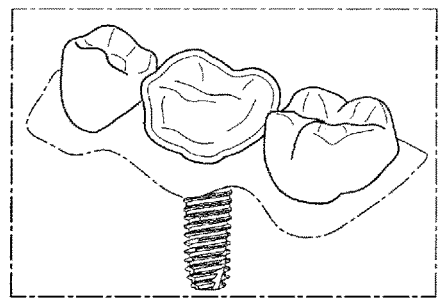
Figure 4:
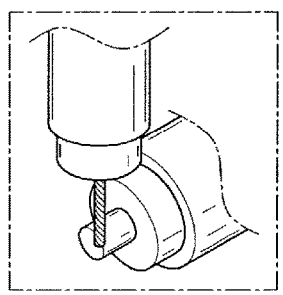
Figure 4:
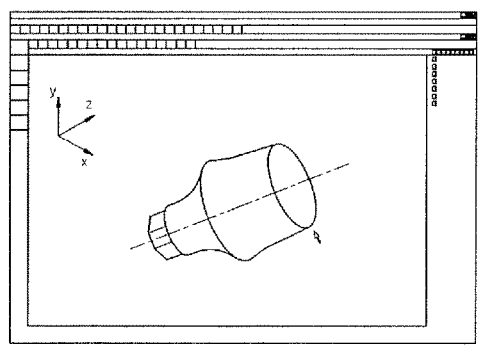
Figure 4:
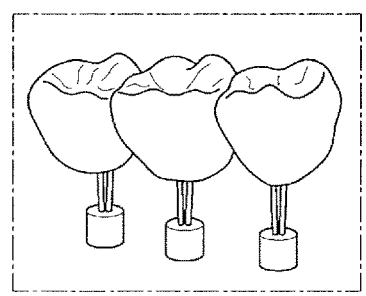
Figure 4:
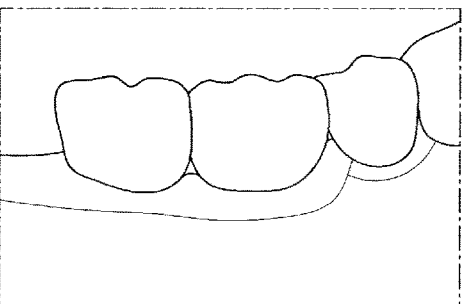
Figure 5:
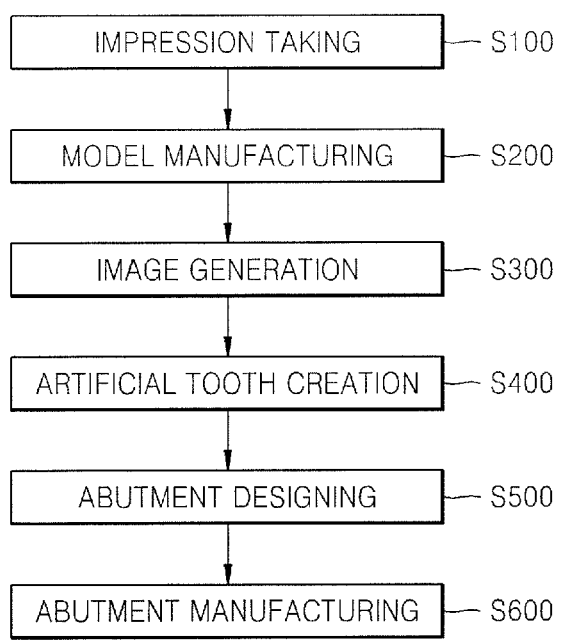
FIG. 5 is a flowchart of a method of manufacturing the dental implant abutment, according to an embodiment of the present invention.

Referring to FIG. 4A, in the image generation S300, a 3D image is generated by scanning the model of the patient's mouth.

In the artificial tooth creation S400, an outer appearance of an artificial tooth is created by using the generated image. Specifically, referring to FIG. 4B, in the artificial tooth creation S400, an outer appearance of a final prosthesis or an artificial tooth is formed based on the generated image, by using a CAD program.

In the abutment designing S500, design information about the abutment is obtained by removing 0.1 to 3 mm of the final artificial tooth or a final abutment along an outer circumferential surface. Specifically, referring to FIG. 4C, the abutment, which includes the concave part 41, in which an overall outer appearance increase upwards and which is recessed inwards, is designed by removing 0.1 to 3 mm of the outer appearance of the final prosthesis.

In the abutment manufacturing S600, referring to FIG. 4D, the dental implant abutment 10 is manufactured by cutting a base material according to the design information about the dental implant abutment 10. Specifically, the abutment manufacturing S600 includes transmitting the design information about the dental implant abutment 10 to a CAM program; creating numerical control (NC) data for tooling the dental implant abutment 10 by using the CAM program; and cutting the dental implant abutment 10 based on the NC data by using a cutting machine.

After the abutment manufacturing S600, referring to FIG. 4E, the porcelain prosthesis 50, which is formed of porcelain, is directly coupled to the manufactured abutment 10, by using a sintering or attachment method.

After the porcelain is bonded to the dental implant abutment 10, a structure, in which the dental implant abutment 10 is covered with the porcelain, is finished as shown in FIG. 4F. The dental implant abutment 10 has an outer circumferential surface that includes a side and an upper surface. The porcelain prosthesis 50 is attached to the outer circumferential surface, and the concave part 41, which is inwardly recessed, is formed on the side of the outer circumferential surface. A horizontal cross-sectional area of the dental implant abutment 10 increases upward from the concave part 41.

With regard to the dental implant abutment 10 according to an embodiment of the present invention, unlike a conventional abutment, an inner crown is formed as one body with the dental implant abutment 10, without having to manufacture an additional inner crown. Therefore, overall work time may be reduced, and a manufacturing cost may be saved. Additionally, since a cast method is not used for manufacturing the inner crown, the manufacturing may not fail and it is easy to manufacture an artificial tooth with consistent quality regardless of the skill of a worker. Particularly, since a possibility of environment pollution, which may be caused in a casting process, is prevented, the dental implant abutment 10 may be manufactured in an environment-friendly way. The dental implant abutment 10, according to an embodiment of the present invention, may be modified as follows:

For example, the second part 30 is shown to be disposed on the first part 20, but is not limited thereto. According to a structure of a fixture, the first part 20 may be formed inside the second part 30.

Additionally, the porcelain may not directly contact the third part 40 and, instead, may be indirectly coupled to the third part 40 by using an additional adhesive.

The present invention is not limited thereto, and the claims of the present invention may be broadly interpreted, if reasonably interpreted, along with the full range of equivalents to which the claims are entitled.

The invention claimed is:

1. A dental implant assembly comprising a fixture, and a dental implant abutment and a porcelain prosthesis, wherein the dental implant abutment is formed as one body and supports the porcelain prosthesis for an outer appearance of an artificial tooth and fixedly couples with the fixture, the dental implant abutment comprising:
 a first part having a coupling structure that corresponds to an inner structure of the fixture, so that the first part couples to the fixture;
 a second part that extends upward from the first part and is adapted to contact gums; and
 a third part extending upward from the second part, having an outer circumferential surface which comprises a side and a top surface, with the porcelain prosthesis attached to the outer circumferential surface, and comprising a shape in which a concave part, inwardly recessed, is formed in the side and a horizontal cross-sectional area increases in an upward direction from the concave part,
 wherein an outer diameter of the second part increases continuously from the first part to the third part, and
 wherein the third part has a shape in which a horizontal cross-sectional area increases in a downward direction from the concave part, and a maximum horizontal cross-sectional area of the third part above the concave part is greater than a maximum horizontal cross-sectional area of the third part below the concave part and,
 wherein the distance between the outer surface of the third part and an outer surface of the porcelain prosthesis is kept constant from the top surface of the third part to the side surface of the third part, and
 wherein the maximum horizontal cross-sectional area of the third part above the concave part is greater than a maximum horizontal cross-sectional area of the second part.

2. The dental implant assembly of claim 1, wherein the third part has an asymmetric outer appearance.

3. The dental implant assembly of claim 1, wherein the porcelain prosthesis and the third part are directly attached to each other in a porcelain furnace by using a sintering process.

4. The dental implant assembly of claim 1, wherein an outer appearance of the third part is manufactured by using a computer-aided design (CAD) program.

5. The dental implant assembly of claim 1, wherein the coupling structure comprises a connection part that has a cross-section in the form of one from among an octagon, a hexagon, a rectangle, and a circle.

6. The dental implant assembly of claim 1, wherein the dental implant abutment is formed of one material from among titanium (Ti), a Ti alloy, a cobalt (Co)-chrome (Cr)-molybdenum (Mo) alloy, a nickel (Ni)—Cr alloy, a gold (Au) alloy, zirconium (Zr), aluminum (Al) oxide, and a polymer.

7. The dental implant assembly of claim 1, wherein a boundary between the second part and the third part has a curved structure.

8. The dental implant assembly of claim 1, wherein a shape of the third part is formed manually by using dental wax and is obtained by using three-dimensional (3D) scanning.

9. The dental implant assembly of claim 1, wherein a shape of the third part is defined by a shape of an artificial tooth.

10. The dental implant assembly of claim 1, wherein the porcelain prosthesis is manufactured by using a method of being sintered and attached to the third part.

11. The dental implant assembly of claim 1, wherein the first part has a flat tapered shape in which an outer diameter decreases from an upper part to a lower part of the first part.

12. The dental implant assembly of claim 11, wherein the upper part has the flat tapered shape and the lower part is the coupling structure for inserting into the fixture, and a step is formed in the outer surface between the upper part and the lower part.

13. The dental implant assembly of claim 1, wherein an outer surface of the second part includes a curved shape as it extends from the first part to the third part, such that the second part has a convex shape that projects outward.

* * * * *